United States Patent [19]
Granstrom et al.

[11] Patent Number: 5,883,095
[45] Date of Patent: Mar. 16, 1999

[54] FORMULATIONS AND METHODS TO TREAT AND PREVENT EQUINE PROTOZOAL MYELOENCEPHALITIS

[75] Inventors: David Granstrom, Hoffman Estates, Ill.; Thomas Tobin, Lexington, Ky.

[73] Assignee: University of Kentucky Research Foundation, Lexington, Ky.

[21] Appl. No.: 908,257

[22] Filed: Aug. 7, 199

Related U.S. Application Data

[60] Provisional application No. 60/042,473 Mar. 31, 1997. 7

[51] Int. Cl.⁶ .......................... A61K 31/53; A61K 31/505
[52] U.S. Cl. .......................... 514/242; 514/241; 514/275
[58] Field of Search ..................... 514/242, 241, 514/275

[56] References Cited

U.S. PATENT DOCUMENTS

| | | | |
|---|---|---|---|
| 3,933,814 | 1/1976 | Haberkorn et al. | 260/248 NS |
| 3,948,893 | 4/1976 | Aichinger et al. | 260/248 NS |
| 3,966,725 | 6/1976 | Reisdorff et al. | 260/248 NS |
| 3,970,752 | 7/1976 | Aichinger et al. | 424/249 |
| 4,952,570 | 8/1990 | Boeckx et al. | 514/242 |
| 4,968,795 | 11/1990 | Lindner et al. | 544/182 |
| 5,114,938 | 5/1992 | Lindner et al. | 514/242 |
| 5,141,938 | 8/1992 | Lindner et al. | 514/242 |
| 5,196,562 | 3/1993 | Lindner et al. | 558/404 |
| 5,214,043 | 5/1993 | Lindner et al. | 514/242 |
| 5,219,853 | 6/1993 | Voege | 514/241 |

OTHER PUBLICATIONS

Vanparijs et al., 129 *Vet. Rec.* 339 (1991).
Mundt, 60 *Vet. Med. Rev.* 16 (1989).
Lindsay et al., 55 *Am. J. Vet. Res.* 976 (1994).
Lindsay et al., 81(2) *J. Parisitol.* 315 (1995).
Dubey and Lindsay, 67 *Vet. Parisitol.* 1 (1996).
Driessen et al., 72 *Aust. Vet.* 139 (1995).
Vanparijs et al., 32 *Vet. Parisitol.* 109 (1989).
Hackstein et al., 81 *Parisitol.. Res.* 207 (1995).

*Primary Examiner*—Phyllis G. Spivack
*Attorney, Agent, or Firm*—Macheledt Bales & Johnson LLP; Kristine H. Johnson

[57] ABSTRACT

The present invention provides formulations useful to treat EPM. It also provides methods to treat EPM in a horse in need of such treatment, comprising administering a pharmaceutically effective amount of a triazine-based anticoccidial. Preferred are methods to treat EPM using clazuril, diclazuril, toltrazuril or letrazuril. The present invention also provides methods to prevent *S. neurona* infection in horses comprising administering a prophylactic amount of a triazine-based anticoccidial. Preferred is a method to prevent *S. neurona* infection by using clazuril, diclazuril, toltrazuril or letrazuril, alone or in combination with other known therapeutics.

11 Claims, No Drawings

FORMULATIONS AND METHODS TO TREAT AND PREVENT EQUINE PROTOZOAL MYELOENCEPHALITIS

BACKGROUND OF THE INVENTION

Equine Protozoal Myeloencephalitis (EPM) is the leading infectious neurologic disease of American horses. Consistently safe and effective treatments for this disease are not available. Conventional therapy relies on relatively non-specific drug/medication combinations; these approaches are only partially effective and relapses and/or adverse reactions are common.

EPM is a New World disease and is the most common infectious neurological disease of horses in the Western hemisphere. It is caused by an "apicomplexan" parasite called *Sarcocystis neurona* (*S. neurona*), which cycles naturally between opossums and birds. The horse is an aberrant host, becoming exposed when it consumes infectious material from opossum feces. In the horse, *S. neurona* makes its way to the brain and spinal cord, where it proliferates and causes clinical disease.

The epidemiology and economic significance of *S. neurona* infection is substantial. In endemic areas in the U.S., over 40% of horses are seropositive. Of these, a small percentage are clinically affected. Of animals clinically affected, 30–40% reportedly fail to respond to current therapy, and some of these animals die. Better and more effective prophylactic and therapeutic modalities are required.

The economic loss in performance horse breeding is likely more substantial than the above figures suggest. The figures presented refer to clinically observable infections only. Subclinical infections will show only at the racetrack, where well-bred animals may fail to perform to their genetic potential because of subclinical infection with EPM. While unrecorded, these losses may be significant.

EPM occurs wherever opossums are found. All cases of EPM therefore trace to Western hemisphere exposure, and the incidence of EPM is likely greatest in areas with high opossum populations. However, clinical cases of EPM are found throughout the world, because horses who become infected with *S. neurona* while in opossum territories may be transported elsewhere.

The localization of *S. neurona* in the brain and spinal cord is a critical obstacle to treatment of EPM. The brain and spinal cord are immunologically privileged; as such, immune responses are likely less effective in the brain than elsewhere. Current treatments, as detailed below, do not directly kill *S. neurona;* as such they often fail to effect a "cure." The present treatment method directly kills *S. neurona,* making it dramatically different from previous treatments.

Previous therapy for BPM consists of administration of various combinations of sulfonamides, trimethoprim and pyrimethamine (Daraprim). However, many horses relapse when therapy ceases, probably because the current therapies do not cross the blood/brain barrier reliably and/or attack the organism directly. These agents only hinder proliferation of *S. neurona* and do not kill it. The inability of current treatments to kill *S. neurona* likely contributes to the significant relapse rate after therapy ceases.

One of the major concerns about current therapeutic approaches to EPM is the difficulty in maintaining simultaneous minimum inhibitory concentrations (MICs) of pyrimethamine, trimethoprim and sulfonamides in the CNS. Because of the uncertainty of the oral bioavailability and steady state concentrations of these agents in the CNS, and the fact that other treatment regimens may be only apicomplexistatic, the availability of a highly lipid-soluble agent with a long plasma half-life, good CNS entry characteristics, and the ability to kill *S. neurona* in the CNS would be a useful addition to the anti-EPM therapeutic armamentarium. Additionally, current therapeutic approaches are associated with significant adverse responses in treated animals, one of which is dysbacteriosis resulting in lethal diarrhea and anemia. A more effective and less toxic agent would be highly desirable. The present invention provides these features, whereas the previous treatments do not The present treatment methods utilize triazine-based anticoccidials, preferably diclazuril, to prevent and treat EPM, without the side effects of previous EPM treatments. EPM and coccidiosis are both caused by "apicomplexan" parasites; however, coccidiosus does not affect the CNS as does EPM.

Triazine-based compounds have previously been used in the prophylaxis of coccidiosis in poultry in Canada, Europe, and South America. Vanparijs et. al., 129 *Vet. Rec.* 339 (1991); Driessen et. al., 72 *Aust. Vet.* 139 (1995). Diclazuril has been used to treat coccidiosus in turkeys, ducks, quail, guinea-fowl, pheasants, partridges, mice, rats, dogs, rabbits, cattle, and horses. Lindsay et al., 55 *Am. J. Vet. Res.* 976 (1994); Lindsay et al., 81(2) *J. Parisitol.* 315 (1995); and Vanparijs et al., 32 *Vet. Parisitol.* 109 (1989). U.S. Pat. No. 4,952,570 also discloses the use of triazine-based compounds (including diclazuril) to treat protozoal infections, although neither Equine Protozoal Myelitis nor *S. neurona* are mentioned. Moreover, diclazuril, in particular is generally considered non-absorbable by the small intestine, and systemic treatment of protozoal infections not possible.

Diclazuril has been shown to be active against *Neospora caninum,* another apicomplexan organism, in vitro but not yet in vivo. Lindsay et. al., 55 *Amer. V et. J. R.* 926 (1994) and Dubey and Lindsay, 67 *Vet. Parisitol.* 1 (1996). Diclazuril has also been shown to be effective against intestinal *Eimeria spp.* in many avian hosts and against intestinal and hepatic coccidiosis in rabbits. Vanparijs et. al., 32 *Vet. Parisitol.* 109 (1989).

In other work, diclazuril has been used in the prophylaxis and treatment of experimental *T. gondii* infection in mice. While diclazuril alone or in combination with pyrimethamine protected mice against death following inoculation with *T. gondii,* diclazuril, alone or in combination did not prevent tissue cyst formation, including brain tissue cyst formation in surviving mice. Based on this work in mice, Lindsay concluded that combinations of diclazuril and pyrimethamine may be beneficial in the treatment of toxoplasmosis in man and animals Lindsay et. al., 81(2) *J. Parisitol.* 315 (1995). More importantly, the mice in these experiments died from pneumonia and hepatitis; there is no evidence from the Lindsay experiments to suggest that diclazuril is effective in the treatment of encephalitis. The data show that diclazuril did not prevent tissue cyst formation in the CNS.

SUMMARY OF THE INVENTION

It is therefore an object of the present invention to provide formulations and methods to prevent or treat EPM comprising administering a pharmaceutically acceptable amount of a triazine-based anti-coccidial such as clazuril, diclazuril, toltrazuril or letrazuril. Treatments and formulations which include a combination of other therapies with the presently-disclosed therapy for treatment of active infection are also within the scope of the present invention.

Definitions:

"EPM" means equine protozoal myelitis or equine protozoal myeloencephalitis or a disease which manifests as symptoms of either equine protozoal myelitis or equine protozoal myeloencephalitis, or closely related apicomplexan-based neurological diseases of horses.

DETAILED DESCRIPTION OF THE INVENTION

The present invention provides formulations of triazine-based anticoccidials for the use in preventing and/or treating EPM. For preventative therapy, a horse-feed based formulation is preferred. Most preferred is a horse-feed formulation which comprises diclazuril. For treatment of clinical or sub-clinical EPM, an oral formulation is preferred. A most preferred oral formulation is one which is administered as a paste. Specifically, an oral formulation which comprises a triazine-based anticoccidial, is administered as a paste, and further comprises other desirable therapeutics, such as anti-inflammatories, sulfonamides, trimethoprim, pyrimethamine and/or other anti-protozoals is considered within the scope of the present invention.

The present invention also provides methods to treat EPM in a horse in need of such treatment, comprising administering a pharmaceutically acceptable amount of a triazine-based anti-coccidial. Preferred is a method to treat EPM using clazuril, diclazuril, toltrazuril or letrazuril. Most preferred is a method to treat EPM using toltrazuril or diclazuril. Also preferred is a method to treat EPM using a triazine-based anti-coccidial in combination with an anti-inflammatory agent and/or previously-known treatment modalities.

Moreover, since horses are a dead-end host for *S. neurona*, triazine-based anticoccidials may be administered prophylactically to horses likely to come in contact with the organism, without the risk of producing a triazine-based anti-coccidial-resistant *S. neurona* in the environment. Therefore, the present invention also provides methods to prevent *S. neurona* infection in horses comprising administering a prophylactic amount of a triazine-based anticoccidial. Preferred is a method to prevent *S. neurona* infection by administering clazuril, diclazuril, toltrazuril or letrazuril. Most preferred is a method to prevent *S. neurona* infection using toltrazuril or diclazuril.

The treatments provided are able to completely kill all *S. neurona* present in the animal. A considerable portion of the recovery from the clinical symptoms of infection, however, occurs after treatment, because clearance of dead *S. neurona* organisms, reduction of inflammatory response and repair of damaged neurons normally takes up to a year. Exercise and anti-inflammatory medication play a positive role in the repair process.

In order to diagnose a horse with clinical EPM, it should be both CSF positive for *S. neurona* antibodies and show a history and clinical signs consistent with EPM. Other non-*S. neurona*-based causes of neuropathy must also be excluded. A further sign is response and/or relapse following standard therapy, if the information is available.

The following is provided as a guideline for diagnosing EPM, although those in the art are familiar with differential diagnosis techniques. Moreover, treatment of mis-diagnosed horses pursuant to the present methods would not result in resistant *S. neurona* for reasons previously discussed. A horse with EPM tends to show the following clinical/clinical chemistry signs:

The horse will: be grade 3–4 on a five point scale neurological exam; asymmetric in muscle vitality; positive for EPM on spinal tap by Western blot, have exhibited relapse after current treatment, with all other potential causes of ataxia excluded.

The triazine-based anticoccidials can be purchased from commercial sources, such as Janssen Pharmaceutica in Belgium (clazuril, letrazuril and diclazuril) or Bayer AG in Leverkusen, Germany (toltrazuril). However, one skilled in the art is aware how to synthesize these compounds de novo using conventional methods.

Formulations can be made using conventional formulation technology. Horse food composition is well known in the art. The present formulation comprises adding at least one triazine-based anti-coccidial to the feed as it is made or after it is made, so as to provide an overall composition consistent with the dosages necessary for prophylaxis or treatment, depending on the use. For instance, for a feed which would be useful as a prophylactic treatment, the following formulation could be made (all percentages are by weight, not less than the numbers given):

| | |
|---|---|
| Diclazuril | 0.0002–0.002% |
| protein | 10% |
| fat | 3.5% |
| fiber | 6.0% |
| calcium | 0.6% |
| phosphorus | 0.45% |
| copper | 35 ppm |
| zinc | 140 ppm |
| selenium | 0.6 ppm |
| vitamin A | 3,000 IU/lb |

A feed which would be useful as a treatment of clinical EPM, could have the following composition, for instance:

| | |
|---|---|
| Toltrazuril | 0.1–0.5% |
| protein | 10% |
| fat | 3.5% |
| fiber | 6.0% |
| calcium | 0.6% |
| phosphorus | 0.45% |
| copper | 35 ppm |
| zinc | 140 ppm |
| selenium | 0.6 ppm |
| vitamin A | 3,000 IU/lb |

However, a preferred embodiment of a feed formulation for treating EPM would be:

| | |
|---|---|
| Diclazuril | 0.25% |
| protein | 10% |
| fat | 3.5% |
| fiber | 6.0% |
| calcium | 0.6% |
| phosphorus | 0.45% |
| copper | 35 ppm |
| zinc | 140 ppm |
| selenium | 0.6 ppm |
| vitamin A | 3,000 IU/lb |

Simple oral formulations may also be made using available Clinacox, oats and molasses, or Clinacox, oats, sweet feed, bran and water, for example. Moreover, any formulation which comprises a triazine-based anti-coccidial and prior EPM treatment methods is considered within the scope of the present invention. For example, sulfonamides, trimethoprim and pyrimethamine (Daraprim) added to the above formulations are within the purview of the present invention. Of course, the formulation would have to be adjusted for the appropriate pharmaceutically-acceptable percentage of final concentration of all ingredients.

Moreover, since paste formulations are the generally preferred mode of administration of orally-bioavailable compounds, a paste formulation acceptable to horses is hereby provided. Any carriers or excipients, preferably those which enhance absorption, can also be included in the present formulations. One such absorption-enhancing carrier is lactose. Other carriers known in the art may also be used. Sweetners or other flavor-enhancers may be used as well.

Some examples of suitable carriers, excipients and diluents include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water syrup, methyl cellulose, methyl-and propylhydroxybenzoates, talc, magnesium stearate and mineral oil. The formulations can additionally include lubricating agents, wetting agents, emulsifying and suspending agents, preserving agents, sweetening agents or flavoring agents. The formulations may be made so as to provide quick, sustained or delayed release of the active ingredient after administration to the patient by employing procedures well known in the art.

The formulations are preferably formulated in a unit dosage form, each dosage containing from about 0.1 to 10% active ingredient by weight, more usually about 0.25 to 5% of the active ingredient. The term "unit dosage form" refers to physically discrete unites suitable as unitary dosages for mammals, each unit containing a predetermined quantity of active material calculated to produce the desired therapeutic effect, in association with a suitable pharmaceutical carrier.

Formulations of the present invention could therefore also contain acceptable amounts of the following ingredients: grain products, molasses products, plant protein products, soybean oil, calcium carbonate, salt, attapulgite clay, dicalcium phosphate, sodium selenite, propionic acid, choline chloride, tetrasodium pyrophosphate, calcium pantothenate, vitamin E supplement, riboflavin supplement, vitamin B-12 supplement, niacin supplement, vitamin A supplement, vitamin D-3 supplement, ferrous carbonate, manganous oxide, zinc oxide, copper sulfate, magnesium oxide, calcium iodate and cobalt carbonate.

These compounds may be administered in any formulation which allows EPM to be treated. For feed formulations, it is important to give enough feed to the animal to ensure ingestion of the required dose. For example, it is necessary to take into account wasted feed that is left in the feeding area and inaccessible to the animal. Moreover, the compounds and/or formulations may be administered via any acceptable method or route. For example, the compounds and/or formulations may be administered in the feed, through formulation with the feed, or via liquid or solid (ie. powder) added at the time of feeding. The compounds and/or formulations can also be administered intravenously, transdermally, sublingually, transmucosally, via tablet, pill, powder, lozenge, sachet, cachet, elixir, suspension, emulsion, solution, syrup, aerosol (as a solid or in a liquid medium), ointment, soft or hard gelatin capsule, suppository, sterile injectable solution, sterile packaged powder and transdermal patch.

The dosage for treatment of EPM will preferably vary according to the weight of the horse (ie. 3–15 mg/kg/day, preferably 5–10 mg/kg/day), for from 20–40 days or longer if required, but can be administered in the following common dosage range: 1.5–10 grams of drug per day. However, any EPM-effective dose or duration of treatment is within the scope of the invention. Moreover, the dosage can be time release, which can be any of the above, except that it is formulated so as to release a certain dose continuously or intermittently over a period of time. It is also a preferred embodiment to administer the drug as an injection, one or more times per day, at the same dose as above.

Because diclazuril has a relatively long plasma half-life in horses, it takes about 5–7 days of a standard 5 mg/kg/21 day treatment for the blood and cerebro-spinal fluid concentrations of diclazuril to attain steady-state. The present invention includes a method to treat EPM wherein steady-state is acheived by administering larger doses ("loading doses") in the first day or first few days of treatment. For example, it may be beneficial to give 5–10 grams per day for the first day or first few days to severely affected horses to attain steady state concentrations quicker than at lower concentrations. Not all horses will require such an accelerated treatment, although such treatment for all horses would not be damaging for those who do not require it.

The dosage for prophylaxis of EPM can be less than that necessary for treating EPM, but may be the same, depending on the need of the individual horse. A typical preventative dose of the triazine-based anti-coccidials herein disclosed would be 0.3–0.15 mg/kg/day, preferably 0.5–0.1 mg/kg/day, however, it can be administered via a feed formulation of 0.0002%–0.002% active ingredient, or 1 mg/kg$^{-1}$ in feed or 200 g of 0.5% Clinacox pre-mix per ton of feed as well. Horses can be fed formulations herein described on a schedule consistent with their needs.

In summary, a full treatment plan for an animal with EPM would comprise the following sequential approaches: a.) reduce of the local inflammatory response in the CNS; b.) kill the *S. neurona* in the CNS; and c.) provide nerve-strengthening stimulus. In order to reduce the local inflammatory response, NSAID medication is effective; especially if started two days before the triazine-based anti-coccidial is started. Banamine, phenylbutazone or similar drugs seem to be optimal. In order to kill S. Neurona, 2.5 grams of diclazuril per day for three weeks seems to be sufficient and may be optimal. In some severe cases, it may be appropriate to give higher doses initially, to increase the rate of steady-state concentrations, or to give larger doses (ie. 2.5–7.5 grams per day) for a longer period of time (ie. 1 to 2 weeks). To optimize neuromuscular circuit function, exercise seems to speed recovery. Daily roundpen exercise and having the animal turned out as much as possible will be beneficial in most cases, so long as the animal tolerates it. Further either steroidal or non-steroidal anti-inflammatory medication during recovery may also be beneficial.

EXAMPLES

Example 1

The Disposition And Pharmacokinetics Of Toltrazuril.

The following were initial studies to determine the bioavailability of toltrazuril in non-EPM infected horses. Five horses were given 5 grams/1000 lbs body weight toltrazuril by stomach tube and blood levels were determined at various time periods after administration.

Toltrazuril was very well-absorbed after administration, with peak plasma concentrations occurring at 24 hours after drug administration. Additionally, this agent was shown to have a long plasma half-life (54 hours). The long plasma half life facilitated maintainenance of plasma concentrations at consistently high ($\mu$g/ml) concentrations for weeks. Under these conditions of continuous high plasma concentrations, the opportunity for the drug to enter the CNS was maximized. Pharmacokinetic projections based on these kinetics were that single daily doses of 5 gms/horse will yield plasma concentrations of about 30 μg/ml of toltrazuril after 15 days. Administered every second day, this same dose yields steady state plasma concentrations of about 15 μg/ml.

Example 2

This trial involved a 12 year old mare with a chronic relapsing case of EPM. This mare was admitted to the Dept. of Clinical Medicine at a major Mid-Western University Teaching Hospital with an admitting diagnosis of severe neurologic dysfunction. The mare was mildly depressed and "shaky", with ataxia, severe proprioceptive deficits and numerous superficial bruises and abrasions. A cerebrospinal fluid analysis was "positive" for antibodies to S. neurona. Based on the clinical symptoms, a presumptive diagnosis of EPM was made. Treatment consisted of oral pyrimethamine (0.3 mg/kg, sid; Daraprim) and trimethoprimsulfamethoxazole (15 mg/kg, bid) and intravenous DMSO with fluids for three days.

The mare was discharged with a diagnosis of EPM with presumptive secondary trauma at the second cervical vertebra. It was recommended that treatment continue for 30 to 60 days. Prior to discharge, the horse had great difficulty walking, and when exiting the stall she reared and fell on her poll. Phenylbutazone was prescribed, presumably for the local trauma and to reduce the inflammatory response in the CNS.

A year later, this horse was shipped to Kentucky. She was accepted as an experimental donation at the University of Kentucky. The mare was sufficiently neurologically impaired so that she was confined to a stall. She could not fend for herself at pasture with other horses, was unable to graze, could not walk in a straight line, and was rapidly losing condition. Later, the mare was severely ataxic, very weak and partially spastic, showing little flexion of the hocks and difficulty in pivoting. This mare was both serum and CSF "positive" for S. neurona on Western blot analysis at the time of donation to UK. Following a neurological examination, the mare was diagnosed as a classic severe, progressive case of EPM. The condition of the mare was deteriorating and she was considered a significant challenge for any therapeutic agent.

After 21 days of treatment with Clinacox (0.5% premix (5g/kg of feed (2.5 g/day)) Pharmacia & Upjohn Animal Health, 40 Centennial Road, Orangeville, Ontario, LDW 3T3) there was a marked amelioration of neurological signs and a concomitant improvement in physical condition. At the end of the treatment, the mare showed some neurologic regression, and the clinical condition was not as good as earlier in the treatment. Treatment was stopped 21 days after start due to lack of available Clinacox. Despite the partial regression in clinical signs in the later phases of therapy the condition of this mare has steadily improved since treatment ceased.

Eighty-three days after the end of treatment, the mare was clinically sound, active and fending for herself in pasture. Although some muscle atrophy and minor signs of permanent neurologic damage remain, the mare has shown no sign of relapse since treatment ceased nine months ago. This mare however, has not gone "CSF negative" for S. neurona, and when tested three months post treatment, she was still CSF positive for antibodies to this agent Nevertheless, since treatment ceased, the clinical condition of this mare has continued to improve and no clinical signs suggestive of relapse or re-infection with S. neurona have been observed. Twelve months after treatment ended, this mare was returned to an experimental breeding herd on the UK farm, essentially neurologically normal. Additionally, this mare has not relapsed or re-infected, despite being in an infectious environment. Clinically, and effectively, this mare continues to improve and has shown no signs of relapse. At twelve months post treatment, this mare is clinically sound and her most recent CSF tap suggest that the amount of anti- S. neurona antibody in her CSF is declining. This mare is likely to go CSF negative for S. neurona eventually.

Example 3

A four year old gelding was treated for 3 weeks with Clinacox as indicated in Example 2. The horse was a grade 3.5 neurological (on scale of 1–5, 5 most severe) when admitted, but had deteriorated prior to treatment Shortly after treatment started, he fell in his stall, could not get up, and had to be slung. He completed the three weeks treatment at 2.5 g of diclazuril/day as Clinacox and remained in the sling for several weeks thereafter. At times, this horse was so weak that euthanasia was seriously considered. However, since treatment ended, he has improved dramatically, presumably due reduction in the inflammatory response and to nerve regeneration once the organism was eliminated. He was turned out in a paddock, and was last graded as 1.5 on the neurological scale. Six months after treatment ceased (July 1997) this gelding has continued to improve and has not relapsed.

Example 4

A fourteen year old mare, about grade 3, had relapsed on previously-known therapies. She was recently admitted, and given three weeks diclazuril, through Clinacox, as above. Her condition improved considerably during treatment and her post-treatment progress is being closely watched. Five months after treatment ended this mare has not relapsed.

Example 5

A valuable two-year old colt in training was admitted at grade 3 on the neurological scale. This horse was unusual in that its symptoms included several cranial nerve signs, indicating that at least some of its EPM lesions were in the brain. Prior to treatment, this animal had difficulty ambulating and leaned against the stall wall; prognosis for this animal was extremely guarded. This animal showed clear clinical improvement by the end of the first week of treatment, at which time light round pen exercise was started. At the end of the second week, light exercise under a rider was started. Administration of diclazuril was continued for a fourth week in this animal because of its training schedule.

Four months after therapy ceased, this animal has improved from grade 3 neurological (barely able to stand), to mild signs on one hind limb. This colt continues to improve daily and has shown no signs of relapse, and has returned to full training.

Example 6

Four 10,000 pound mares were dosed with 500 g Clinacox (2.5 g diclazuril) by stomach tube and plasma concentrations of the agent were followed. Plasma concentrations of Clinacox peak at about 1.0 μg/ml at 24 hours after dosing and decline with a half-life of about 45 hours. Pharmacokinetic projections based on these data show that daily oral doses of Clinacox should yield steady state plasma concentrations of diclazuril by six days after dosing and that trough plasma concentrations of diclazuril are not less than 85% of peak plasma concentrations.

These consistently high plasma concentrations of diclazuril, the apparently high oral bioavailability of this agent and its apparently high lipid solubility makes it extremely likely that therapeutically significant cerebrospinal fluid concentrations of this agent in animals are attained and maintained on the standard therapeutic schedule.

More recently, CSF concentrations of 200–250 mg/ml diclazuril in horses have been detected. These findings of significant steady state concentrations of diclazuril in CSF support and extend the examples of oral bioavailability of these agents, their ability to penetrate the central nervous system and their apparent therapeutic efficacy in the treatment of equine protozoal myeloencephalitis.

What is claimed is:

1. A method to treat EPM in a horse is need of such treatment, comprising administering a pharmaceutically effective amount of a triazine-based anti-coccidial.

2. A method of claim 1, wherein the triazine-based anti-coccidial is chosen from the group consisting of clazuril, diclazuril, toltrazuril and letrazuril.

3. A method of claim 1, wherein the triazine-based anti-coccidial is toltrazuril.

4. A method of claim 1, wherein the triazine-based anti-coccidial is diclazuril.

5. A method of claim 4, which further comprises administering a pharmaceutically-effective anti-inflammatory agent.

6. A method of claim 5, which further comprises exercising the horse daily.

7. A method to prevent *S. neurona* infection in horses comprising administering a prophylactic amount of a triazine-based anticoccidial.

8. A method of claim 7, wherein the triazine-based anticoccidial is chosen from the group consisting of clazuril, diclazuril, toltrazuril and letrazuril.

9. A method of claim 8, wherein the triazine-based anticoccidial is diclazuril.

10. A method to kill *S. neurona* in horses comprising administering *S. neurona*-killing amount of diclazuril.

11. A horse-feed formulation useful to treat equine protozoal myeloencephalitis comprising a triazine-based anticoccidial and an anti-protozoal agent selected from the group consisting of: sulfonamide, trimethoprim and pyrimethamine.

* * * * *